United States Patent [19]

McFadden

[11] 4,221,867
[45] Sep. 9, 1980

[54] OPTICAL MICROBIOLOGICAL TESTING APPARATUS AND METHOD

[75] Inventor: Francis J. McFadden, Lake Elmo, Minn.

[73] Assignee: Minnesota Mining and Manufacturing Company, St. Paul, Minn.

[21] Appl. No.: 8,933

[22] Filed: Feb. 2, 1979

[51] Int. Cl.² ............................................. C12Q 1/18
[52] U.S. Cl. ........................................ 435/32; 435/29; 435/34; 435/39; 435/287; 435/808; 350/276 SL; 350/89; 356/244; 356/441
[58] Field of Search ................... 435/4, 7, 29, 32, 33, 435/34, 39, 40, 287, 808; 356/337, 441, 244; 350/89, 276 R, 276 SL

[56] References Cited

U.S. PATENT DOCUMENTS

| Re. 27,617 | 4/1973 | Olsen | 350/276 R X |
|---|---|---|---|
| 3,356,462 | 12/1967 | Cooke et al. | 422/102 |
| 3,441,383 | 4/1969 | Moore et al. | 422/102 |
| 3,652,169 | 3/1972 | Danti et al. | 356/244 |
| 3,712,746 | 1/1973 | Bergeron | 356/244 X |
| 3,919,559 | 11/1975 | Stevens | 250/508 |
| 4,055,470 | 10/1976 | Sheaff et al. | 435/34 X |
| 4,099,881 | 7/1978 | Vanden Broek et al. | 356/244 X |

Primary Examiner—Robert J. Warden
Attorney, Agent, or Firm—Cruzan Alexander; Donald M. Sell; James V. Lilly

[57] ABSTRACT

A device for determining the susceptability of microorganisms, i.e., bacteria, to antibiotics is provided. The device utilizes a layer of light transmissive material having a plurality of flat, opaque louver elements set in a transparent matrix which permit transmission of visible light and illumination of a sample being tested. A method for determining the susceptability is also provided.

13 Claims, 7 Drawing Figures

OPTICAL MICROBIOLOGICAL TESTING APPARATUS AND METHOD

BACKGROUND OF THE INVENTION

This invention relates to a microbiological testing apparatus and method of use. More particularly, it relates to a device and method for determining the minimum concentration of antibiotics necessary to inhibit the growth of microorganisms, i.e., bacteria. This concentration is sometimes referred to hereinafter as the minimum inhibitory concentration.

The large number of strains of highly pathogenic bacteria and their varying susceptability to antibiotics has resulted in the development of microtitration techniques for determining the minimum inhibitory concentration. These techniques typically involve the use of microtitration plates which comprise, for example, a one-piece, plastic shell containing a plurality of recepticals or incubation wells. The wells may be arranged in parallel rows such as is described in U.S. Pat. No. 3,356,462, or in a circular pattern such as is described in U.S. Pat. No., 3,441,383. In any event, during the test, the wells contain the microorganism to be inhibited, nutrient broth and antibiotic. Typically each of the wells contains a different concentration of antibiotic. The contents of the wells are incubated for a period of time and are then studied so as to determine the minimum inhibitory concentration of the antibiotic.

In the past the determination of minimum inhibitory concentration has been made by illuminating the incubated wells and then viewing the contents either directly from above or indirectly by observing a reflected image of the contents. Those wells which contain a sufficient concentration of antibiotic to inhibit the growth of the microorganisms contain a clear solution, while those wells which contain an insufficient concentration of antibiotic have either a turbid solution or a small turbid area or dot surrounded by clear solution therein.

It is frequently difficult to determine when the contents of the incubated wells comprise a clear solution. This is especially true when the contents are either lightly turbid or a small turbid dot surrounded by clear solution. Accordingly, it would be highly desirable to provide a device and process which enhances the visibility of the contents of the incubation wells and simplifies the ability to determine the minimum inhibitory concentration.

SUMMARY OF THE INVENTION

The present invention provides a device and method which significantly enhances the visibility of the contents of the incubation wells. This substantially reduces the possibility that an improper concentration of antibiotic will be selected as the minimum inhibitory concentration for failure to correctly observe the contents of the wells. The present invention also provides a device and method which assists the operator in rapidly determining the minimum inhibitory concentration.

These advantages are achieved by the use of a layer of light transmissive material which provides "dark field illumination" (described more fully hereinafter) to illuminate an incubation well while providing a contrasting dark background against which the illuminated well is observed. Additionally, the light transmissive layer provides a band of directed light which illuminates the entirety of an incubation well and minimizes the amount of extraneous refracted light striking that well.

In accordance with the present invention, there is provided a device for determining the minimum concentration of antibiotic necessary to inhibit the growth of microorganism in an elongate incubation well which contains the microorganism and a nutrient broth, said device comprising:

(a) a light transmissive layer;
(b) a light source capable of emitting visible light on one side of said layer;
(c) means for positioning an elongate incubation well containing nutrient broth, microorganism and an antibiotic on the other side of said layer;

said light transmissive layer having a plurality of flat, opaque louver elements set in a transparent matrix so as to permit transmission of said visible light along lines generally parallel to said louver elements, said layer directing transmitted light to said incubation wells at an intersect angle of no less than about 20° with respect to the elongate axis of said incubation well.

Also provided herein is a method for determining the minimum inhibitory concentration of said antibiotic. This method comprises the steps of placing a microtitration plate having at least one elongate incubation well which contains the microorganism, antibiotic and a nutrient broth on the above described device such that the microtitration plate is on said means for positioning;

directing light through the opaque, louver elements of the light transmissive layer of said device and illuminating the incubation well;

viewing the illuminated incubation well; and determining the minimum concentration of antibiotic necessary to inhibit the growth of the microorganism.

BRIEF DESCRIPTION OF THE DRAWINGS

The present invention is described in more detail hereinafter with reference to the accompanying drawings wherein like reference characters refer to the same parts throughout the several views and wherein.

DESCRIPTION OF THE PREFERRED EMBODIMENTS

Figure 1:
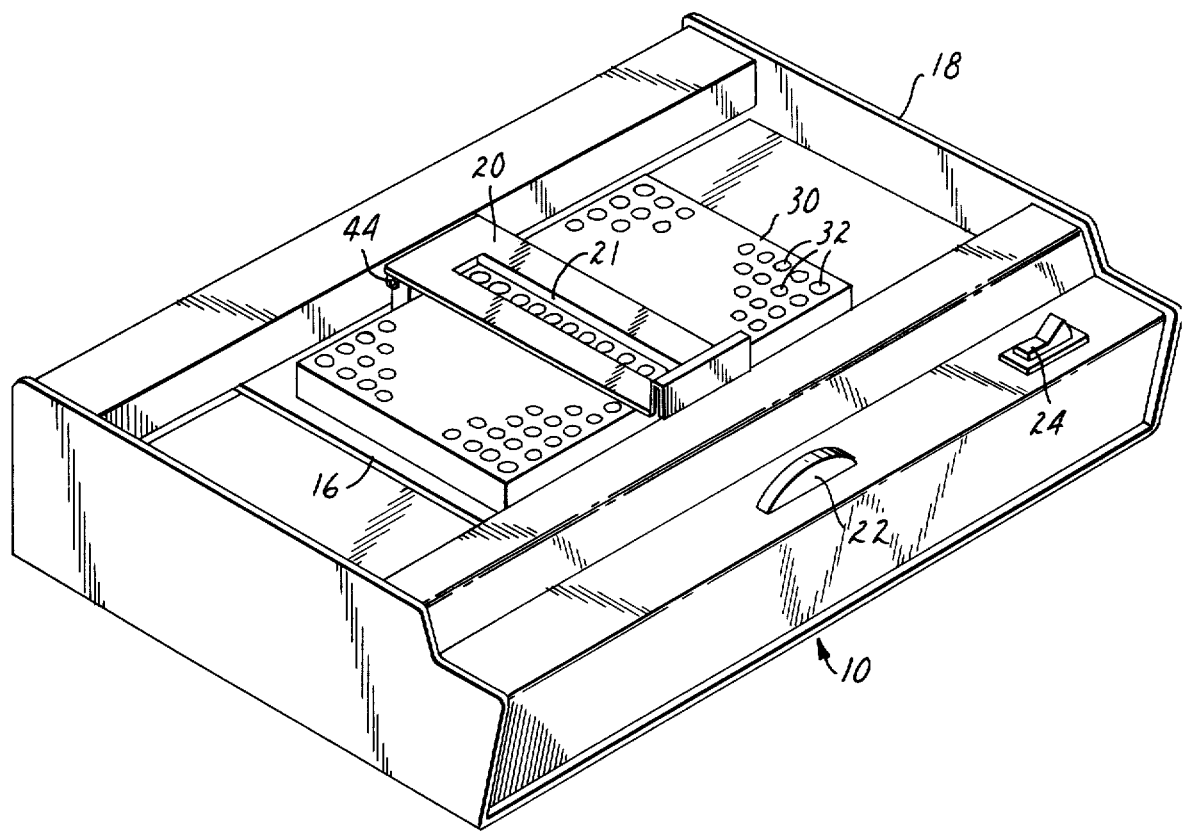
FIG. 1 is a left-front perspective view of one embodiment of the device of the present invention.
Figure 2:
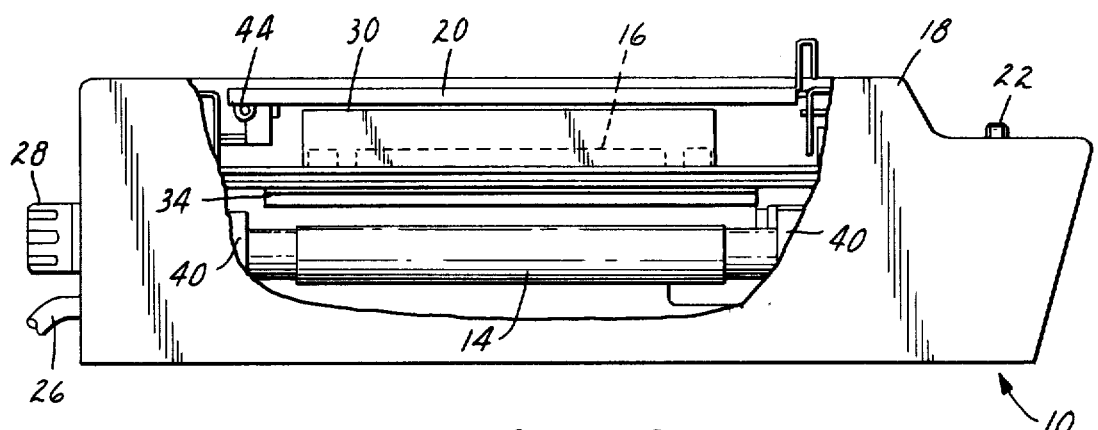
FIG. 2 is an elevation view, partially in section, of the left side of the device of FIG. 1.
Figure 3:
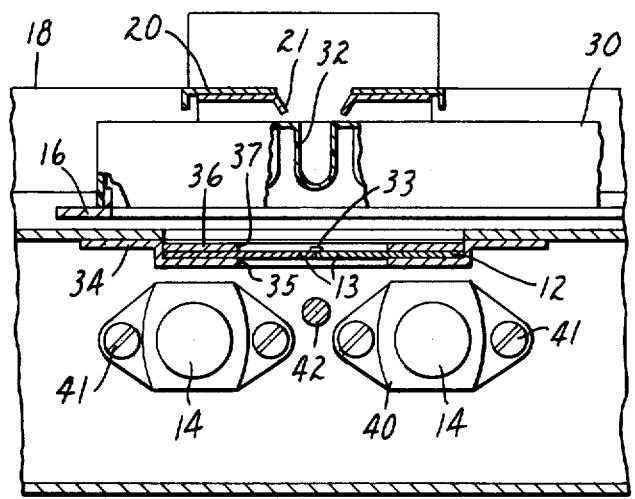
FIG. 3 is an elevation view, partially in section, of the back of the device of FIG. 1.

Referring now specifically to the drawings, FIGS. 1, 2 and 3 show a device 10 according to the present invention. Device 10 comprises a light transmissive layer 12 (see FIG. 3), a light source 14 capable of emitting visible light on one side of layer 12 (see FIGS. 2 and 3), and a positioning means 16 on the other side of layer 12 for positioning an incubation well containing nutrient broth, microorganism and antibiotic. In the embodiments illustrated, device 10 further includes a housing 18, a screen 20 through which an incubation well, or a row of incubation wells may be seen and a rotatable means 22 for advancing or reversing position means 16. Additionally, device 10 further includes a power switch 24, a power cord 26, and a fuse receptable 28.

FIGS. 1-3 also show a microtitration plate 30 on positioning means 16. Microtitration plate 30 has a plurality of parallel rows of uniformly arranged elongate incubation wells 32 therein.

In the embodiment described in FIGS. 1-3, light transmissive layer 12 is disposed above light source 14 by means of supports 34 and 36. These supports sandwich light transmissive layer 12 therebetween and maintain layer 12 in a fixed position in the device of the present invention. The supports 34 and 36 are not transmissive to light emitted from source 14. However, they are provided with apertures 35 and 37 respectively which permit light emitted from source 14 to pass through light transmissive layer 12 and illuminate incubation wells 32. The supports 34 and 36 shown in FIGS. 2 and 3 comprise a metal. However they can also comprise any other material which prevents the transmission of light such as opaque plastic, wood, etc.

Light transmissive layer 12 comprises a sheet of material having a plurality of flat, opaque louver elements 13 which are set in a transparent matrix 15. The louver elements 13 are set at an angle $\theta$ with respect to the faces of layer 12. Angle $\theta$, sometimes referred to hereinafter as the angle of asymmetry, of louver elements 13 permits layer 12 to be transparent to visible light along lines generally parallel to said louver elements. However, angle $\theta$ prevents layer 12 from being transparent to visible light along lines not generally parallel to said louvered elements.

The net effect is to provide a source of "dark-field illumination" wherein light 17 transmitted through layer 12 illuminates incubation wells 32 yet provides a dark, contrasting background against which the wells 32 are seen when viewed perpendicularly from above layer 12. This greatly enhances the visibility of the contents of wells 32.

Figure 4:
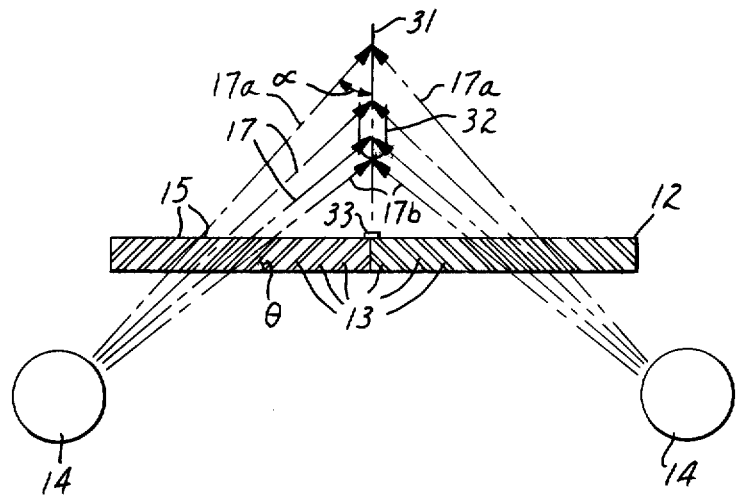
FIGS. 4, 5, 6 and 7 are schematic views of representative configurations of useful light transmissive layers and light sources.

The foregoing is illustrated in FIGS. 4-7, thus, light source 14 provides visible light 17 which passes through matrix 15 of layer 12. Louver elements 13 of layer 12 permit only the transmission of light 17 which is generally parallel to the angle of asymmetry of said louver elements and which intersects the elongate axis 31 of wells 32 at an intersect angle of $\alpha$ of no less than about 20°. This is accomplished by preferably spacing the louver elements 13 such that the opposed edges of adjacent louvers overlap as is shown in FIG. 4. However, alternative means may be employed to prevent the transmission of light through layer 12 which would intersect the elongate axis 31 of wells 32 at an angle of less than 20°. Thus, a mask 33 (See FIGS. 3, 5 and 6) may be employed to block out such light.

As can be seen by reference to FIGS. 4-7, all of the light 17 transmitted through layer 12 is not strictly parallel to the angle of asymmetry of said louver elements. Thus this light can have an angle larger than the angle of asymmetry as is represented by light 17a in FIG. 4 or, alternatively it can have an angle smaller than the angle of asymmetry as is represented by light 17b in FIG. 4. However, even though the transmitted light may vary slightly in angle, it is considered to be generally parallel to said angle of asymmetry.

Preferably, the louver elements 13 have an angle of asymmetry in the range of from about 30° to 60°. Most preferably they have an angle of asymmetry of about 45°. It is also preferred that the angle of asymmetry be the same for all louver elements 13 in a given layer 12.

Figure 5:
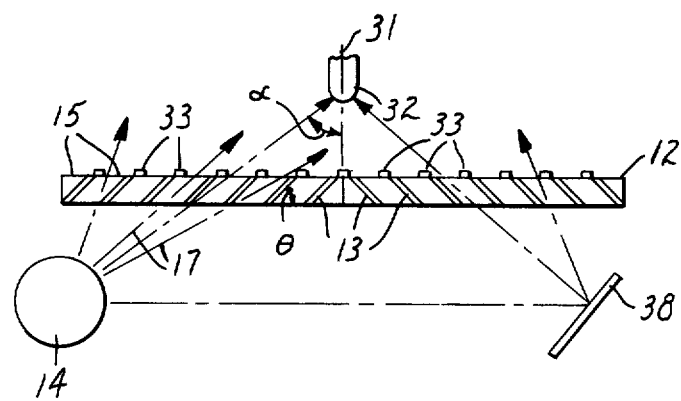

As is shown in FIGS. 3-7, light transmissive layer 12 may have a variety of configurations. Thus, as is shown in FIGS. 3-5, light transmissive layer 12 may comprise two sections of light transmissive material having a plurality of flat, opaque louver elements 13 set in a transparent matrix 15. The two sections of light transmissive material are oriented with respect to each other such that the transmitted light strikes incubation well 32 from opposite sides of elongate axis 31. In these embodiments it is preferable to provide a mask 33 along the juncture of the two sections of light transmissive layer 12.

Figure 6:
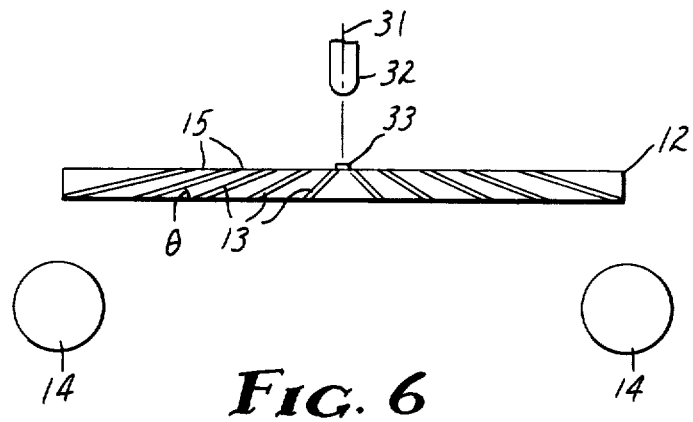
Figure 7:
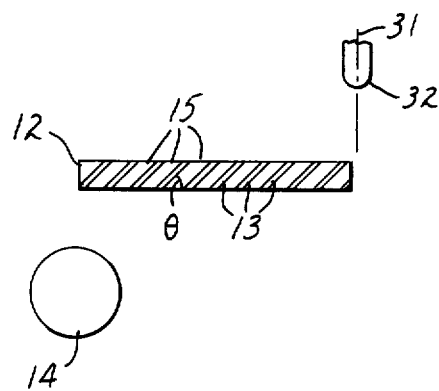

Other configurations of light transmissive layer 12 are shown in FIGS. 6 and 7. Thus, light transmissive layer 12 may comprise a single section of light transmissive material which has a plurality of flat, opaque louver elements 13 set in a transparent matrix 15. FIG. 6 further demonstrates that the angle of asymmetry of the lower elements may either vary or be constant within layer 12. In those embodiments where the angle of asymmetry of louver elements 13 would permit transmitted light to strike incubation wells 32 at an intersect angle $\alpha$ of less than about 20° with respect to elongate axis 31, or where the louver elements 13 are spaced such that the opposed edges of adjacent louvers do not overlap, a mask 33 is provided on layer 12 which prevents the transmission of light which would intersect the elongate axis 31 of incubation wells 32 at an angle of less than about 20°. See FIGS. 5 and 6.

Processes for preparing materials useful as the light transmissive layer in the present invention are known. They are described, for example, in U.S. Pat. Nos. RE 27,617 and 3,919,559. Such materials are also commercially available from the Minnesota Mining and Manufacturing Company as "Light Control Film". Other materials are also useful as the light transmissive layer and will be obvious to those skilled in the art as a result of this disclosure.

The light source 14 which emits visible light can be selected from a variety of light sources. However, it has been found that cylindrical flourescent lights are particularly useful in the device of the present invention as such sources provide a uniform source of visible light across the entirety of layer 12.

At least one light source 14 is employed in the device of the present invention. However, as is shown in FIGS. 3, 4 and 6, two light sources 14 may be employed. Alternatively, as is shown in FIG. 5, one light source 14 may be employed in conjunction with a reflecting device 38. The reflecting device may be of any configuration provided that it redirects the light 17 emitted from source 14 through and along lines generally parallel with the louver elements 13 of layer 12.

In the embodiment shown in FIGS. 1, 2 and 3, light source 14 is held in position by means of holders 40. Holders 40 are in turn fastened to housing 18 by means of screws 41.

In the most preferred aspect of the present invention the minimum concentration of antibiotic necessary to inhibit the growth of a microorganism is determined in a microtitration plate 30 which has a plurality of parallel rows of uniformly arranged elongate incubation wells 32 therein. Wells 32 may have any of a variety of geometric configurations. However, it is preferred that they be cylindrical. It is also preferred that microtitration plate 30 be movable on positioning means 16. This is accomplished by means of an arrangement of gears (not shown) which connect rotatable means 22 to positioning means 16 via rotatable shaft 42. Rotatable means 22 may be moved to the left or the right thereby advancing or reversing the position of microtitration plate with respect to light transmissive layer 12.

It is also preferred that a screen 20 be provided over microtitration plate 30. Screen 20 has an opening 21 therethrough which permits one row of incubation wells 32 to be viewed while blocking those immediately adjacent thereto from view. This aids the operator in focusing on the row of incubation wells 32 then being observed. Screen 20 is preferably hingably fixed on one end thereof to housing 18 by means of hinge 44.

The distance of each of the elements from each other, i.e., the distance of light source 14 to light transmissive layer 12 and the distance of the light transmissive layer 12 to incubation wells 32, may be varied. However, as the distance from light source 14 to light transmissive layer 12 increases, it is necessary to increase the distance of light transmissive layer 12 to the row of incubation wells 32 so as to achieve the optimum illumination of said incubation wells by said light source. Thus, it is preferred that these distances be kept to a minimum so as to achieve maximum illumination in the minimum amount of space.

The device and method of the present invention are conveniently used to determine the minimum inhibitory concentration. Thus in one method, a microtitration plate 30, preferably having a plurality of parallel rows of elongate incubation wells 32, is provided. In this method, each of the wells 32 contains, in dehydrated form, the antibiotic to be tested. Each well 32 has a different amount of antibiotic therein so that upon rehydration each contains a different concentration of antibiotic. Separate rows of wells 32 may also contain different antibiotics if it is desired to determine the susceptability of a microorganism to more than one antibiotic.

The incubation wells 32 are rehydrated with a suitable nutrient broth, each receiving the same amount of broth. The wells 32 are then inoculated with a standard amount of the microorganism to be tested and incubated.

In the most preferred aspect of the invention, the microtitration plate 30 contains at least two wells 32 which are employed for sterility control and growth control in addition to those wells employed for determining the minimum inhibitory concentration. The well employed for sterility control contains only nutrient broth. It contains no antibiotic and is not inoculated with microorganism. Consequently, if any growth occurs in this well, it is an indication that the plate 30 has been contaminated and that any readings obtained therefrom may be incorrect.

The well employed for growth control contains nutrient broth and is inoculated with microorganism. This well receives no antibiotic. If growth of microorganism does not occur in this well, it is an indication that the plate 30 may be defective and that readings obtained therefrom may be incorrect After rehydration, inoculation and incubation, the plate 30 is placed on positioning means 16 and, preferably, screen 20 is placed thereover. Light source 14 is then activated and the light 17 emitted therefrom is retransmitted through the matrix portions 15 of light transmissive layer 12 along lines generally parallel to the angle of asymmetry of louver elements 13. The transmitted light intersects the elongate axis 31 of wells 32 and illuminates the contents thereof.

The operator observes the illuminated wells from above, preferably through screen 20, and notes those wells which contain clear solution and the concentration of antibiotic therein. This concentration generally constitutes the minimum inhibitory concentration. However, if all concentrations of a given antibiotic produce clear solutions then it is possible that a lower concentration may be the minimum inhibitory concentration. If, on the other hand, none of the concentrations of antibiotic produce clear solutions, then a higher concentration may be the minimum inhibitory concentration.

Rotatable means 22 is employed to advance or reverse the position of plate 30. Thus the operator can easily view each of the rows of incubation wells in any order desired.

While the foregoing description has been directed to a manually operated device for determining the minimum inhibitory concentration, it is also possible to provide the device in an automatic form. An automatic device greatly increases the speed with which determination of the minimum inhibitory concentration may be made and provides a method by which a printout of the results may be obtained.

The embodiments of the present invention described hereinabove represent only a few of said embodiments. Still others are possible as will be understood by those skilled in the art and are included within the scope of the following claims.

What is claimed is:

1. A device for determining the minimum concentration of antibiotic necessary to inhibit the growth of microorganism in an elongate incubation well which contains the microorganism and a nutrient broth, said device comprising:
   (a) a light transmissive layer
   (b) a light source capable of emitting visible light on one side of said layer
   (c) means for positioning an elongate incubation well containing nutrient broth, microorganism and antibiotic on the other side of said layer,
   said light transmissive layer having a plurality of flat, opaque louver elements set in a transparent matrix so as to permit transmission of said visible light along lines generally parallel to said louver elements, said layer directing transmitted light to said incubation well at an intersect angle no less than about 20° with respect to the elongate axis of said incubation well.

2. A device in accordance with claim 1 wherein said light transmissive layer directs said transmitted light to said incubation well from opposite sides of the elongate axis of said well.

3. A device in accordance with claim 1 wherein said flat, opaque louver elements have an angle of asymmetry in the range of from about 30° to 60°.

4. A device in accordance with claim 3 wherein said angle of asymmetry is about 45°.

5. A device in accordance with claim 1 wherein said light transmissive layer comprises two sections of light transmissive material having a plurality of flat, opaque louver elements set in a transparent matrix, said sections of light transmissive material being oriented with respect to each other such that said layer directs said transmitted light to said incubation well from opposite sides of said elongate axis.

6. A device in accordance with claim 5 wherein said flat, opaque louver elements have an angle asymmetry in the range of from 30° to 60°.

7. A device in accordance with claim 6 wherein said angle asymmetry is about 45°.

8. A device in accordance with claim 5 further comprising a microtitration plate on said means for positioning, said microtitration plate having a plurality of parallel rows of uniformly arranged elongate incubation wells therein.

9. A device in accordance with claim 8 wherein said light transmissive layer generally directs said transmitted light to a single row of said incubation wells and illuminates said row.

10. A device in accordance with claim 9 further comprising a screen over said microtitration plate, said screen having an opening therethrough for viewing said illuminated row of incubation wells.

11. A device in accordance with claim 10 wherein said flat, opaque louver elements have an angle of asymmetry in the range of from about 30° to 60°.

12. A device in accordance with claim 11 wherein said angle of asymmetry is about 45°.

13. A method for determining the minimum concentration of an antibiotic necessary to inhibit the growth of a microorganism in an elongate incubation well comprising the steps of:

placing a microtitration plate having at least one elongate incubation well which contains the microorganism, antibiotic and a nutrient broth on the device of claim 1 such that said microtitration plate is on said means for positioning;

directing light through the opaque, louver elements of the light transmissive layer of said device and illuminating said incubation well;

viewing said illuminated incubation well; and determining the minimum concentration of antibiotic necessary to inhibit the growth of the microorganism.

* * * * *